United States Patent [19]

Cetenko et al.

[11] Patent Number: 5,290,800
[45] Date of Patent: Mar. 1, 1994

[54] 3,5-DI-TERTIARYBUTYL-4-HYDROXY-PHENYLMETHYLENE DERIVATIVES OF 2-SUBSTITUTED THIAZOLIDINONES, OXAZOLIDINONES, AND IMIDAZOLIDINONES AS ANTIINFLAMMATORY AGENTS

[75] Inventors: Wiaczeslaw A. Cetenko; David T. Connor; Jagadish C. Sircar; Roderick J. Sorenson; Paul C. Unangst, all of Ann Arbor, Mich.

[73] Assignee: Warner-Lambert Company, Morris Plains, N.J.

[21] Appl. No.: 896,299

[22] Filed: Jun. 10, 1992

Related U.S. Application Data

[60] Division of Ser. No. 640,711, Jan. 18, 1991, Pat. No. 5,143,928, which is a continuation-in-part of Ser. No. 499,937, Mar. 19, 1990, abandoned.

[51] Int. Cl.$^5$ .................. C07D 203/40; A61K 31/42
[52] U.S. Cl. ................................. 514/376; 548/226; 548/228
[58] Field of Search ................. 548/226, 228; 514/376

[56] References Cited

U.S. PATENT DOCUMENTS

| 4,241,073 | 12/1980 | Jamieson et al. |
| 4,345,072 | 8/1982 | Kleemann et al. |
| 4,582,903 | 4/1986 | Mirviss |
| 4,650,876 | 3/1987 | Mirviss |
| 5,208,250 | 5/1993 | Cetenko .................. 514/369 |

FOREIGN PATENT DOCUMENTS

| 0037480 | 10/1981 | European Pat. Off. |
| 861062495 | 12/1986 | European Pat. Off. |
| 0211670 | 2/1987 | European Pat. Off. |
| 863061347 | 2/1987 | European Pat. Off. |
| 0304493 | 3/1989 | European Pat. Off. |
| 0343643 | 11/1989 | European Pat. Off. |
| 0391644 | 10/1990 | European Pat. Off. |
| 62-29570 | 3/1987 | Japan. |
| 2078218A | 1/1982 | United Kingdom. |

OTHER PUBLICATIONS

Chemical Abstracts, vol. 105, No. 11, Sep. 15, 1986 Katsumi I., et al. "Studies on Styrene Derivatives..." Chem. Abstract No. 90791x.
Derwent Abstr. No. 86-059691/09.
Derwent Abstr. No. 86-460104-B.
Derwent Abstr. No. 88-178973/26.
Derwent Abstr. No. 87-076383/11.
Derwent Abstr. No. 87-076379/11.
Derwent Abstr. No. 87-087608/13.
Derwent Abstr. No. 86-295746/45.
Derwent Abstr. No. 88-199351/29.

Primary Examiner—Robert Gerstl
Attorney, Agent, or Firm—Ronald A. Daignault; Elizabeth M. Anderson

[57] ABSTRACT

The novel 3,5-ditertiarybutyl-4-hydroxy-phenylmethylene derivative of 2-substituted thiazolidinones, oxazolidinones, and imidazolidinones as antiinflammatory agents having inhibiting activity for 5-lipoxygenase, cyclooxygenase, or both.

11 Claims, No Drawings

3,5-DI-TERTIARYBUTYL-4-HYDROXYPHENYL-METHYLENE DERIVATIVES OF 2-SUBSTITUTED THIAZOLIDINONES, OXAZOLIDINONES, AND IMIDAZOLIDINONES AS ANTIINFLAMMATORY AGENTS

This is a divisional application of U.S. Ser. No. 07/640,711, filed Jan. 11, 1991, now U.S. Pat. No. 5,143,928, which is a continuation-in-part of U.S. application Ser. No. 07/499,937, filed Mar. 27, 1990, now pending.

BACKGROUND OF THE INVENTION 3,5-Di-tertiarybutyl-4-hydroxyphenyl derivatives of 2-substituted thiazolidinones, oxazolidinones, and imidazolidinones are disclosed as a moiety in a variety of compounds.

For example, U.S. application Ser. No. 07/198,528, filed May 25, 1988, now abandoned; U.S. application Ser. No. 07/334,346, filed Apr. 10, 1989, now abandoned; and U.S. application Ser. No. 07/375,794, filed Jul. 5, 1989 disclose thiazolidinones, imidazolidinones, and oxazolidinones including 3,5-di-t-butyl-4-phenol. In fact, the disclosures in the Background of the Invention of U.S. application Ser. No. 07/198,528, filed May 25, 1988, now abandoned; U.S. application Ser. No. 07/334,346, filed Apr. 10, 1989, now abandoned; and U.S. application Ser. No. 07/375,794, filed Jul. 5, 1989 cites other disclosures and therefore they are incorporated here by reference. However, the present compounds differ from this disclosure by the 2-substituent of each of the thiazolidinone, oxazolidinone, or imidazolidinone ring systems.

Other references disclose compounds having the 2-substituents of the present invention with various other rings such as thiadiazoles, oxadiazoles or triazoles. See U.S. application Ser. No. 07/277,171, filed Nov. 29, 1988, now abandoned, and U.S. application Ser. No. 07/426,814, filed Oct. 30, 1989, now pending. However, such references differ from the present invention in both the heteroaryl ring moiety and the substituent between the heteroaryl ring and the 3,5-ditertiarybutyl-4-hydroxyphenyl moiety. The present invention is limited to rings linked by a methylene moiety.

SUMMARY OF THE INVENTION

The present invention is a novel compound of the formula I

I and a pharmaceutically acceptable base or acid addition salt thereof; in which
Me is methyl;
X is S, O, NH or N-lower alkyl;
$R_8$ is hydrogen or methyl;
Y is $SCH_3$, $SOCH_3$, $SO_2CH_3$, $NR_1R_2$, NHCN, $$\underset{NHCNHR_3}{\overset{Z}{\|}} \quad \underset{NHNHCNH_2,}{\overset{S}{\|}} \quad \underset{NHNHCNH_2,}{\overset{NH}{\|}} \quad N(OR_6)R_4,$$

-continued $$N(OH)COR_5, \quad NR_4W, \quad \underset{CH_3}{\overset{CH_3}{|}}CHCO_2R_4,$$

$(CH_2)_mCO_2R_4$, $S(CH_2)_nCO_2R_6$, or $NR_7COR_6$
wherein
Z is O, S, NH, NCN
W is $CO_2R_7$ wherein $R_7$ is as defined herein, $$\underset{CH_3}{\overset{CHCO_2H,}{|}}$$

n is 1, 2, 3 and
m is 1 to 5;
$R_1$, $R_2$ are independently H, lower alkyl, arylalkyl, or $(CH_2)_nNR_6R_7$
$R_3$ is H, alkyl or aryl;
$R_4$ is H or alkyl;
$R_5$ is alkyl, aryl, or $CF_3$;
$R_6$ is H or lower alkyl; and
$R_7$ is lower alkyl.
The present invention is also a novel compound of the formula II

II or a pharmaceutically acceptable base or acid addition salt thereof;
wherein X is S, O, NH or N-loweralkyl; and
$Y^1$ is OH or SH.
The present invention is also a pharmaceutical composition for treating a disease or condition, such as rheumatoid arthritis, osteoarthritis, other inflammatory conditions, psoriasis, allergic diseases, inflammatory bowel disease, GI ulcers, cardiovascular conditions including ischemic heart disease and atherosclerosis, and ischemia-induced cell damage, particularly brain damage caused by stroke, preferably an inflammatory disease or condition, comprising an antiinflammatory, antipsoriatic, antiallergy, antiulcer, antiischemic, antiatherosclerotic, or cytoprotective amount of the compound of the formula I or II or a pharmaceutically acceptable salt of I or II as defined above and a pharmaceutically acceptable carrier.

The present invention is also a method of treating a disease or condition as noted above in a mammal, particularly a human, suffering therefrom which comprises administering a compound of the formula I or II or salt of I or II as defined above in unit dosage form.

The invention also provides for use of any such compound of formula I or II or salt of I or II in the manufacture of a medical therapeutic agent.

The pharmaceutical composition or method of treating which is the present invention is meant to include what is understood to be prophylactic to one of a foregoing named disease or condition.

The compounds of the formula I or II have activity as inhibitors of 5-lipoxygenase, cyclooxygenase or both enzymes to provide the use for the pharmaceutical composition and methods of the present invention.

A preferred compound of the formula I is 5-[[3,5-Bis(1,1-dimethylethyl)-4-hydroxyphenyl]methylene]-2-imino-4-thiazolidinone, (Z)-, methanesulfonate (1:1) salt, 5-[[3,5-Bis(1,1-dimethylethyl)-4-hydroxyphenyl]methylene]-2-(methoxymethylamino)-4(5H)-thiazolone, monohydrochloride, (Z)-, 5-[[3,5-bis(1,1-dimethylethyl)-4-hydroxyphenyl]methylene]-2,4-thiazolidinedione, 2-oxime (Z)-, 5-[[3,5-Bis(1,1-dimethylethyl)-4-hydroxyphenyl]methylene]-2-(methylthio)-4(5H)-thiazolone, (Z)-, 5-[[3,5-Bis(1,1-dimethylethyl)-4-hydroxyphenyl]methylene]-2-[hydroxy(1-methylethyl)amino]-4(5H)-thiazolone, (Z)-, [5-[[3,5-Bis(1,1-dimethylethyl)-4-hydroxyphenyl]methylene]-4,5-dihydro-4-oxo-2-thiazolyl]cyanamide, choline salt, 5-[[3,5-Bis(1,1-dimethylethyl)-4-hydroxyphenyl]methylene]-2-(methylthio)-4(5H)-oxazolone, [5-[[3,5-Bis(1,1-dimethylethyl)-4-hydroxyphenyl]methylene]-4,5-dihydro-4-oxo-2-oxazolyl]cyanamide and 5-[[3,5-Bis(1,1-dimethylethyl)-4-hydroxyphenyl]methylene]-4,5-dihydro-1-methyl-4-oxo-1H-imidazol-2-yl-cyanamide.

More preferred is 5-[[3,5-Bis(1,1-dimethylethyl)-4-hydroxyphenyl]methylene]-2-imino-4-thiazolidinone, (Z)-, methanesulfonate (1:1) salt, 5-[[3,5-Bis(1,1-dimethylethyl)-4-hydroxyphenyl]methylene]-2-(methoxymethylamino)-4(5H)-thiazolone, monohydrochloride, (Z)-, 5-[[3,5-Bis(1,1-dimethylethyl)-4-hydroxyphenyl]methylene]-2-[hydroxy(1-methylethyl)amino]-4(5H)-thiazolone, (Z)- and [5-[[3,5-Bis(1,1-dimethylethyl)-4-hydroxyphenyl]methylene]-4,5-dihydro-4-oxo-2-thiazolyl]cyanamide, choline salt.

Most preferred is 5-[[3,5-Bis(1,1-dimethylethyl)-4-hydroxyphenyl]methylene]-2-imino-4-thiazolidinone, (Z)-, methanesulfonate (1:1) salt and 5-[[3,5-Bis(1,1-dimethylethyl)-4-hydroxyphenyl]methylene]-2-(methoxymethylamino)-4(5H)-thiazolone, monohydrochloride, (Z)-.

A DETAILED DESCRIPTION OF THE INVENTION

In the present invention "lower alkyl" is alkyl of from one to six carbons, inclusive, and means methyl, ethyl, propyl, butyl, pentyl, or hexyl and isomers thereof.

Halogen is chloro, iodo, bromo or fluoro.

Aryl is phenyl unsubstituted or substituted by one, two or three substituents of one or more of each of alkyl of one to four carbons, inclusive, $OR_4$ wherein $R_4$ is independently as defined above, $SR_4$ wherein $R_4$ is independently as defined above,

wherein $R_4$ is independently as defined above, $C(O)OR_4$ wherein $R_4$ is independently as defined above, hydroxymethyl, $NR_6R_7$ wherein $R_6$ and $R_7$ are each independently as defined above, or nitro, or halogen.

Aralkyl is an aryl as defined above and attached through an alkylenyl such as methylenyl, ethylenyl, propylenyl, butylenyl and isomers thereof.

Me is methyl.

The compounds of the invention may contain geometric isomers. Thus, the invention includes the individual isomers and mixtures thereof. The individual isomers may be prepared or isolated by methods known in the art.

A tautomeric form of selected compounds of formula I or II would be recognized by an ordinarily skilled artisan to be within the present invention.

The compounds of formula I or II are useful both in the free base and where possible the free acid form or in the form of base salts thereof, as well as in the form of acid addition salts. All forms are within the scope of the invention. In practice, use of the salt form amounts to use of the acid or free base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; choline; guanidine; N-methylglucosamine; N-methylpiperazine; morpholine; ethylenediamine; N-benzylphenethylamine; tris(-hydroxymethyl) aminomethane; and the like. (See, for example, "Pharmaceutical Salts," *J. Pharm. Sci.*, 66(1), 1-19 (1977).)

The acid addition salts of said basic compounds are prepared either by dissolving the free base of compound I in aqueous or aqueous alcohol solution or other suitable solvents containing the appropriate acid or base and isolating the salt by evaporating the solution, or be reacting the free base of compound I with an acid as well as reacting compound I having an acid group thereon with a base such that the reactions are in an organic solvent, in which case the salt separates directly or can be obtained by concentration of the solution.

The base salts of compounds of formula I or II described above are prepared by reacting the appropriate base with a stoichiometric equivalent of the acid compounds of formula I to obtain pharmacologically acceptable base salts thereof.

The compounds of this invention may also exist in hydrated or solvated forms.

The usefulness of the compounds of the present invention as inhibitors of one of the 5-lipoxygenase enzyme or cyclooxygenase enzyme or both, or in treating related diseases or conditions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2 \times 10^6$ cells/mL. Cells are incubated with and without test agent (in DMSO) (1% DMSO is without effect on arachidonic acid metabolism) for 10 minutes at room temperature. Calcium ionophore A23187 (5 μM) is added and cells are incubated for 7 minutes at 37° C. The reaction is stopped by chilling the tubes on ice for 10 minutes. Cells are separated by centrifugation and the supernatant is stored at $-20°$. Aliquots (100 μL) are analyzed for $LTB_4$ and $PGF_{2\alpha}$ using radioimmunoassay kits as provided by the supplier.

Table I contains biochemical data obtained from this whole cell assay as $IC_{50}$s which are calculated as the amount of test compound causing 50% inhibition or % of inhibition at the named micromoles (μM) of $LTB_4$ or $PGF_{2\alpha}$ formation.

Carrageenan-Induced Rat Foot Paw Edema-2 (CFE-2) Assay: Protocol

Carageenan solution (1% w/v) is prepared by dissolving 100 mg carrageenan (Marine Colloidal Div., Springfield, N.J.) in 10 mL of sterile saline (0.9%) solution (Travenol). The solution is vortexed for 30 to 45 minutes. Animals are dosed with compound 1 hour before carrageenan challenge. Foot paw edema is induced by injecting 0.10 mL of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured 5 hours after carrageenan. The difference between the 5-hour and the initial paw volume is expressed as delta edema. The delta edema for each test group of animals is used to calculate the percent inhibition of edema achieved by the compound at the test dose compared with the vehicle control group. The data in Table I (the dose at which swelling is inhibited by the noted percent) is calculated by probit analysis for the dose at which percent inhibition occurs.

Mycobacterium-Induced Rat Footpad Edema Assay (MFE): Protocol

*Mycobacterium butyricum* (5 mg/mL) is suspended in paraffin oil by sonication for 10 minutes in an ice bath. Footpad edema is induced on Day 0 by injecting 0.1 mL of the Mycobacterium mixture into the left hindpaw of lightly anesthetized rats. Swelling in the injected hindpaw is determined by mercury plethysmography 72 hours after injection. Groups of rats are treated with test compounds (suspended in 0.5% hydroxypropyl methylcellulose with 0.2% Tween-80) or vehicle 1 hour before Mycobacterium injection and on Days 1 and 2. Inhibition of swelling is determined by comparing the change in hindpaw volume in compound- and vehicle-treated rats. An $ID_{40}$ (the dose at which swelling is inhibited by 40%) is calculated by probit analysis or shown as the % inhibition at the dose expressed as μM, i.e., % at μM.

Gastric Ulcerogenicity (UD): Protocol

Male outbred Wistar rats (100–250 g) are fasted for 24 hours. After fasting, test compounds are administered orally (in 2 mL/kg of 0.5% hydroxypropyl methylcellulose) and the rats are denied access to food and water for 6 more hours. The rats are then sacrificed with $CO_2$ so that the stomachs can be removed, opened along the greater curvature, and evaluated for the presence of gastric ulcers. Results are expressed as the percent of rats with gastric ulcers at a given dose or as the $UD_{50}$ (the dose which causes ulcers in 50% of the rats).

TABLE I

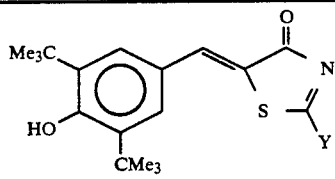

| Example Number | Y | % at μM/ $IC_{50}$ (μM) ARBL | % at μM/ $IC_{50}$ (μM) ARBC | % at μM/ $ID_{40}$ (mg/kg) CFE | % at μM/ $ID_{40}$ (mg/kg) MFE | Gastric Ulcerogenicity $UD_{50}$ |
|---|---|---|---|---|---|---|
| 1B | $NH_2$ | 100% @ $10^b$ | 80% @ $10^d$ | | <10 | N @ $200^e$ |
| 3 | N(CH_3)(OCH_3) | $1.7^a$ | $0.33^c$ | 41% @ 10 | 13.2 | |
| 4 | NHOH | 100% @ $10^b$ | 81% @ $10^d$ | 32% @ $10^d$ 17% @ 30 | | |
| 5 | $SCH_3$ | $0.5/0.8^a$ | $<0.6^c$ | 47% @ 30 | 27% @ 2 | |

TABLE I-continued

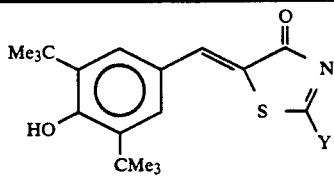

| Example Number | Y | % at μM/ IC$_{50}$ (μM) ARBL | % at μM/ IC$_{50}$ (μM) ARBC | % at μM/ ID$_{40}$ (mg/kg) CFE | % at μM/ ID$_{40}$ (mg/kg) MFE | Gastric Ulcerogenicity UD$_{50}$ |
|---|---|---|---|---|---|---|
| | | | | 36% @ 10 | 23% @ 50 | |
| 12 | CH$_3$<br>\|<br>NH—CHCOOH | 100% @ 10$^b$ | 55% @ 10$^d$ | | | |
| 7 | S<br>\|\|<br>NH—NH—C—NH$_2$ | 0.39$^a$ | 4.55$^c$ | | | |
| 9 | NHCN | 0.63$^a$ | 0.16$^c$ | 49% @ 30<br>32% @ 3 | | |
| 16 | NH<br>\|\|<br>NH—C—NH$_2$ | 100% @ 10$^b$ | 87% @ 10$^d$ | | | |

$^a$IC$_{50}$ for LTB$_4$ inhibition
$^b$% inhibition of LT by @ 10 μM
$^c$IC$_{50}$ for PGF$_2\alpha$
$^d$% inhibition of PGF$_2\alpha$
$^e$N is not active at the dose tested Accordingly, the present invention also includes a pharmaceutical composition for treating one of the above diseases or conditions comprising an antidisease or anticondition effective amount of a compound of the formula I or II or salt thereof as defined above together with a pharmaceutically acceptable carrier.

The present invention further includes a method for treating one of the above named diseases or conditions in mammals, including man, suffering therefrom comprising administering to such mammals either orally or parenterally, preferably oral, a corresponding pharmaceutical composition containing a compounds of the formula I or II or salt thereof.

A physician or veterinarian of ordinary skill readily determines a subject who is exhibiting symptoms of any one or more of the diseases described above. Regardless of the route of administration selected, the compounds of the present invention of the formula I as described in pharmaceutical compositions above are formulated into pharmaceutically acceptable dosage forms by conventional methods known to the pharmaceutical art.

The compounds can be administered in such oral unit dosage forms as tablets, capsules, pills, powders, or granules. They also may be administered rectally or vaginally in such forms as suppositories or bougies; they may also be introduced parenterally (e.g., subcutaneously, intravenously, or intramuscularly) using forms known to the pharmaceutical art. They are also introduced directly to an affected area (e.g., in the form of eye drops or by inhalation). For the treatment of asthma or allergies, particularly dermatological disorders such as erythema, psoriasis, and acne, the compounds may also be administered topically in the form of ointments, gels, or the like. However, in general, the preferred route of administration is orally.

An effective but nontoxic quantity of the compound is employed in treatment. The ordinarily skilled physician or veterinarian will readily determine and prescribe the effective amount of the compound to prevent or arrest the progress of the condition for which treatment is administered. In so proceeding, the physician or veterinarian could employ relatively low dosages at first, subsequently increasing the dose until a maximum response is obtained.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula I or II or pharmacologically acceptable salt thereof to achieve a therapeutic effect will, of course, vary both with the particular compound, the route of administration, the mammal under treatment, and the particular disorder or disease concerned. A suitable dose of a compound of formula I or II or pharmacologically acceptable salt thereof for a mammal suffering from, or likely to suffer from any condition as described hereinbefore is 0.1 μg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 ng to 100 μg of the compound per kilogram, typically about 0.1 μg/kg.

In the case of oral dosing for the treatment or prophylaxis of arthritis or inflammation in general, due to any course, a suitable dose of a compound of formula I or II or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula I or II or a pharmacologically acceptable acid addition or base salt thereof and a pharmacologically acceptable carrier therefor. Such formulations constitute a further feature of the present invention.

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I or II is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivativse;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives' as defined herein are nonnarcotic analgesics/nonsteroidal antiinflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$NA$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$ COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

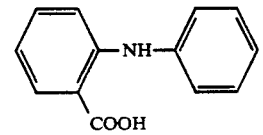

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

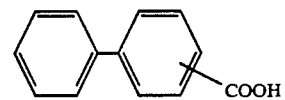

which can bear a variety of substituents and in which the free —COOH group can be in the form of a pharmaceutically acceptable salt group, e.g., —COO—Na$^+$.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

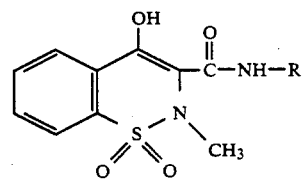

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I or II may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compounds of the formula I or II are prepared generally by the following processes and constitute a further aspect of the present invention.

Generally, the compounds of formula I or II are prepared by one of the following methods.

General Procedure for the Preparation of 3,5-Di-tertbutyl-4-hydroxyphenylmethylene Derivatives of 2-Substituted Thiazolidinones, Oxazolidinones and Immidazolidinones as Antiinflammatory Agents A general method for the preparation of benzylidene compound 2 is the condensation of the thione 1 (Iso Katsumi et al Chem. Pharm. Bull., 34(4);1619–1627 (1986) with amines such as hydroxylamine, N-methyl-hydroxylamine, and N,N-dimethylethylamine in hydroxylic solvents such as methanol, ethanol, isopropanol at temperature 24°–100° C. with the evolution of hydrogen sulfide. Variations in the definition of Y as found in the compound of formula I of the present invention are prepared by processes analogous to those described in U.S. application Ser. No. 426,814 filed Oct. 30, 1989 and published in EP application 89121896.8. which, therefore, is incorporated by reference.

An alternate procedure for the preparation of the above compound 2 is the condensation of methylmercapto compound 3 with amines such as N-isopropylhydroxylamine, N-cyclohexylhydroxylamine, methoxylamine, aqueous methylamine, aqueous dimethylamine, guanidine, thiosemicarbazide in alcoholic solvents at temperature 24°–100° C. with the evolution of methylmarcaptan.

Another procedure for the preparation of the above compound 2 is the condensation of methylmercapto compound 3 with cyanamide, glycine, dl-alanine, 2-cyanoacetamide in hydroxylic solvents such as methanol, ethanol, isopropanol at temperature 40°–100° C. in the presence of potassium t-butoxide.

3,5-di-tert-butyl-4-hydroxy-2-methylmarcapto compound 3, is used as a starting material for a variety of transformations. The compound 3 is synthesized from 1 by reacting with methyliodide in dioxane in the presence of triethylamine at 0°–50° C.

Similar treatment of 1 with isopropyl iodide or bromo acetic acid gives the desired compound 4, where $R=CH(CH_3)_2$, $CH_2CO_2H$

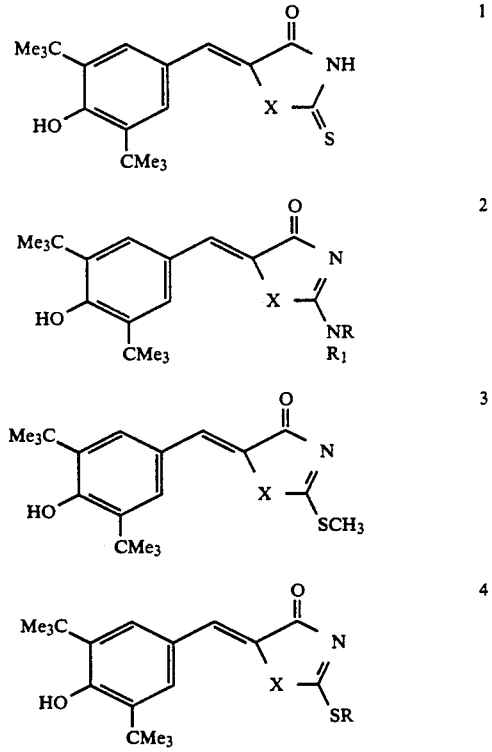

One of skill in the art would recognize variations in the sequence and would recognize variations in the appropriate reaction conditions from the analogous reactions shown or otherwise known which may be appropriately used in the processes above to make the compounds of the formula I or II herein.

Introduction and removal of such suitable oxygen protecting groups are well known in the art of organic chemistry; see for example, "Protective Groups in Organic Chemistry," J. F. W. McOmie, ed., (New York, 1973), pages 43ff, 95ff, J. F. W. McOmie, *Advances in Organic Chemistry*, Vol. 3, 159–190 (1963); J. F. W. McOmie, *Chem. & Ind.*, 603 (1979), and T. W. Greene, "Protective Groups in Organic Synthesis", Wiley (New York), 1981, Chapters 2, 3, and 7.

Examples of suitable oxygen protecting groups are benzyl, trialkylsilyl, ethoxyethyl, methoxyethoxymethyl, methoxymethyl, trialkylsilylethyl, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although such groups may not be expressly illustrated.

The products of the reactions described herein are isolated by conventional means such as extraction, distillation, chromatography, and the like.

Starting materials not described herein are available commercially, are known, or can be prepared by methods known in the art.

The salts of the compounds of formula I or II described above are prepared by reacting the appropriate base or acid with a stoichiometric equivalent of the compounds of formula I or II.

The invention is further elaborated by the representative examples as follows. Such examples are not meant to be limiting.

EXAMPLE 1

5-[[3,5-Bis(1,1-dimethylethyl)-4-hydroxyphenyl]methylene]-2-imino-4-thiazolidinone, (Z)-

A mixture of 3,5-di-tert-butyl-4-hydroxybenzaldehyde (9.4 g, 0.04 mole), pseudothiohydantoin (4.7 g, 0.0405 mole), sodium acetate (8.3 g, 0.1 mole), and glacial acetic acid (200 mL) is stirred and heated at reflux for 21 hours. The cooled mixture is added to ice-water and the precipitated solid is filtered and washed with water. The solid residue is dissolved in ether and washed successively with water, aqueous sodium bicarbonate solution, and water. The extract is dried and the solvent is removed to give 9.4 g of a residue. The crude product is recrystallized from methanol-ethyl acetate to give 3.8 g (38%) of 5-[[3,5-Bis(1,1-dimethylethyl)-4-hydroxyphenyl]methylene]-2-imino-4-thiazolidinone, (Z)-, mp 277°-279° C.

Anal. for $C_{18}H_{24}N_2O_2S$: Calcd: C, 65.03; H, 7.28; N, 8.43; S, 9.64. Found: C, 64.90; H, 7.30; N, 8.21; S, 9.50.

EXAMPLE 1B

5-[[3,5-Bis(1,1-dimethylethyl)-4-hydroxyphenyl]methylene]-2-imino-4-thiazolidinone, (Z)-, methanesulfonate (1:1) salt A solution of methanesulfonic acid (0.75 g, 0.0078 mole) in tetrahydrofuran (4 mL) is added to a stirred solution of 5-[(3,5-bis(1,1-dimethylethyl)-4-hydroxyphenyl)methylene]-2-imino-4-thiazolidinone (2.32 g, 0.007 mole) in tetrahydrofuran (189 mL) at room temperature. The mixture is stirred for 25 minutes and the solvent is removed <30° C. under reduced pressure. The residue is triturated with ether and the resulting solid is collected, washed with ether to give 2.99 g of a solid mp 252° C. (dec). The residue is recrystallized from methanol-ether to give 2.67 g (89.3%) of 5-[[3,5-bis(1,1-dimethylethyl)-4-hydroxyphenyl]methylene]-2-imino-4-thiazolidinone, (Z)-, methanesulfonate (1:1) salt, mp 252° C. (dec).

Anal. for $C_{18}H_{24}N_2O_2S.CH_3SO_3H.0.13H_2O$: Calcd: C, 52.96; H, 6.61; N, 6.50; S, 14.88. Found: C, 52.58; H, 6.57; N, 6.38; S, 14.94.

EXAMPLE 2

5-[[3,5-Bis(1,1-dimethylethyl)-4-hydroxyphenyl]methylene]-2-(hydroxymethylamino)-4(5H)-thiazolone,(Z)-

A mixture of N-methylhydroxylamine hydrochloride (12.52 g, 0.15 mole), barium carbonate (14.8 g, 0.075 mole), ethanol (50 mL), and water (50 mL) is stirred at room temperature for ten minutes. 5-[(3,5-bis (1,1-dimethylethyl)-4-hydroxyphenyl)methylene]-2-thioxo-4-thiazolidinone (see Ikuo Katsumi et al *Chem. Pharm. Bull.*, 34(4), 1619–1627 (1986)) (17.5 g, 0.05 mole) and ethanol (600 mL) are added to it and the resulting mixture is stirred and refluxed for 8 hours. The reaction mixture is then cooled, filtered, and the solvent is removed at 45° C. under reduced pressure. The residue is treated with ice-water and the resulting solid is separated by filtration, washed with water and extracted with methylene chloride. The organic layer is dried and concentrated to give 19 g of a residue. The residue is flash chromatographed over silica gel (214 g), eluting first with methylene chloride and then with methylene chloride-methanol (9:1) to give 11.5 g of the pure product. It is recrystallized from methanol-ethyl acetate, to give 8.6 g (48%) of 5-[[2,6-Bis(1,1-dimethylethyl)-4-hydroxyphenyl]methylene]-2-(hydroxymethylamino)-4(5H)-thiazolone, (Z)-, mp 199°-200° C. (dec).

Anal. for $C_{19}H_{26}N_2O_3S$: Calcd: C, 62.96; H, 7.23; N, 7.73; S, 8.84. Found: C, 62.72; H, 7.23; N, 7.43; S, 8.59.

EXAMPLE 3

5-[[3,5-Bis(1,1-dimethylethyl)-4-hydroxyphenyl]methylene]-2-(methoxymethylamino)-4(5H)-thiazolone, monohydrochloride, (Z)-

A solution of 5-[(3,5-bis(1,1-dimethylethyl)-4-hydroxyphenyl]methylene]-2-(methoxymethylamino)-4(5H)-thiazolone (8.3 g, 0.022 mole) in 50 mL methylene chloride is treated with ethereal hydrogen chloride to give 9.1 g (quantitative yield) of pure product, mp 177°-179° C. It is recrystallized from methylene chloride-methanol-ether to give 6.0 g (66%) of analytically pure 5-[[3,5-bis(1,1-dimethylethyl)-4-hydroxyphenyl]methylene]-2-(methoxymethylamino)-4(5H)-thiazolone, monohydrochloride, (Z)-, mp 177°-179° C.

Anal. for $C_{20}H_{28}N_2O_3S.HCl$: Calcd: C, 58.17; H, 7.08; N, 6.78; S, 7.76; Cl, 8.58. Found: C, 58.60; H, 7.20; N, 6.81; S, 7.85; Cl, 8.31.

EXAMPLE 4

5-[[3,5-bis(1,1-dimethylethyl)-4-hydroxyphenyl]methylene]-2,4-thiazolidinedione, 2-oxime (Z)-

A mixture of hydroxylamine hydrochloride (40.75 g, 0.59 mole), potassium-t-butoxide (60.6 g, 0.54 mole), and methanol (500 mL) is stirred at room temperature for 25 minutes. A solution of 5-[(3,5-bis (1,1-dimethylethyl)-4-hydroxyphenyl)methylene]-2-thioxo-4-thiazolidinone (49.64 g, 0.14 mole) in methanol (2.5 L) is then added and the mixture is stirred and refluxed for 23 hours. The reaction mixture is then cooled, filtered, and the solvent evaporated at 45° C. under reduced pressure. The residue is treated with ice-water and the resulting solid is separated, washed with water, and then dissolved in ether. The organic layer is dried to give 15 g of a solid. The solid is recrystallized from ether-toluene to give 14.6 g (30%) of pure 5-[[3,5-bis(1,1-dimethylethyl)-4-hydroxyphenyl]methylene]-2,4-thiazolidinedione, 2-oxime (Z)-, mp 241° C. (dec).

The compound of Example 4 is also made via $BaCO_3$ method as described in Example 2 using appropriate corresponding starting materials.

EXAMPLE 5

5-[[3,5-Bis(1,1-dimethylethyl)-4-hydroxyphenyl]methylene]-2-(methylthio)-4(5H)-thiazolone, (Z)-

A solution of 5-[(3,5-bis(1,1-dimethylethyl)-4-hydroxyphenyl)methylene]-2-thioxo-4-thiazolidinone (69.9 g, 0.2 mole) and triethylamine (20.24 g, 0.2 mole) in dioxane (1.1 L) is stirred at room temperature for 1 hour. Methyl iodide (141.9 g, 1 mole) is added and the reaction mixture is stirred for additional 20 hours. The mixture is filtered and the excess solvent is removed <40° C. under reduced pressure. The cooled mixture is added to ice-water and extracted with chloroform. The solution is washed with water and concentrated to leave a residue. This residue is recrystallized first from toluene and then from methanol to give 19.2 g (26%) of pure product, mp 159°-160° C. The combined filtrates are evaporated and the residue is recrystallized from methanol to give additional amount of 20.7 g (29%) of the product which is 5-[[3,5-Bis(1,1-dimethylethyl)-4-hydroxyphenyl]methylene]-2-(methylthio)-4(5H)-thiazolone, (Z)-, mp 159°-160° C.

Anal. for $C_{19}H_{25}NO_2S_2$: Calcd: C, 62.77; H, 6.93; N, 3.85; S, 17.64. Found: C, 62.80; H, 6.54; N, 3.47; S, 17.72.

EXAMPLE 6

N-[5-[[3,5-Bis(1,1-dimethylethyl)-4-hydroxyphenyl]methylene]-4-oxo-2-thiazolidinylidene]glycine, (Z)-

A mixture of glycine (2.25 g, 0.03 mole), potassium-t-butoxide (2.81 g, 0.025 mole), and ethanol (700 mL) is stirred at room temperature for 15 minutes. 5-[(3,5-Bis(1,1-dimethylethyl)-4-hydroxyphenyl)methylene]-2-(methylthio)-4(5H)-thiazolone (7.27 g, 0.02 mole) is added to it and the mixture is refluxed with stirring for 20 hours. The mixture is then filtered and the solvent removed at 40° C. under reduced pressure. The residue is treated with ice-water, acidified with 1N aqueous hydrochloric acid and extracted with ether. The organic layer is washed with water, dried, and the solvent removed to give 7.75 g of a solid. The crude solid is recrystallized from tetrahydrofuran-ether to give 2.95 g (38%) of pure N-[5-[3,5-[bis(1,1-dimethylethyl)-4-hydroxyphenyl]methylene]-4-oxo-2-thiazolidinylidene]glycine, (Z)-, mp 260° C. (dec). Anal. for $C_{20}H_{26}N_2O_4S.0.25C_4H_8O$: Calcd: C, 61.74; H, 6.91; N, 6.86; S, 7.85. Found: C, 61.82; H, 7.08; N, 6.50; S, 7.55.

EXAMPLE 7

2-[5-[[3,5-Bis(1,1-dimethylethyl)-4-hydroxyphenyl]methylene]-4-oxo-2-thiazolidinylidene]hydrazinecarbothiamide, (Z)-

A mixture of 5-[(3,5-bis(1,1-dimethylethyl)-4-hydroxyphenyl]methylene]-2-(methylthio)-4(5H)-thiazolone (6.13 g, 0.0169 mole) and thiosemicarbazide (1.53 g, 0.0169 mole) in ethanol (300 mL) is refluxed with stirring for 7 hours. After standing overnight at room temperature, the product is separated by filtration, washed with ethanol to give 5.78 g of a solid. It is recrystallized from DMF-methanol to give 3.4 g (47%) of pure 2-[5-[[3,5-Bis(1,1-dimethylethyl)-4-hydroxyphenyl]methylene]-4-oxo-2-thiazolidinylidene]hydrazinecarbothiamide, (Z)-, mp 200°-202° C.

Anal. for $C_{19}H_{26}N_4O_2S_2.H_2O$: Calcd: C, 53.75; H, 6.65; N, 13.20. Found: C, 53.76; H, 6.48; N, 13.24.

EXAMPLE 8

5-[[3,5-Bis(1,1-dimethylethyl)-4-hydroxyphenyl]methylene]-2-[hydroxy(1-methylethyl)amino]-4(5H)-thiazolone, (Z)-

A mixture of N-isopropylhydroxylamine hydrochloride (5.5 g, 0.049 mole), potassium-t-butoxide (4.83 g, 0.043 mole), and ethanol (500 mL) is stirred at room temperature for 15 minutes. 5-[(3,5-Bis(1,1-dimethylethyl)-4-hydroxyphenyl)methylene]-2-(methylthio)-4(5H)-thiazolone (7.27 g, 0.02 mole) is then added and the mixture is refluxed with stirring for six hours. After removal of the solvent under reduced pressure, the cooled reaction mixture is poured into a mixture of ice-water containing 1N hydrochloric acid and extracted with ether. The organic layer is washed with water, dried, and the solvent is evaporated to give 7.7 g of a residue. The residue is flash chromatographed on silica gel (202 g), eluting first with methylene chloride and then with methylene chloride-methanol (9:1) to give 7.0 purified product. It is recrystallized from methylene chloride-ethyl acetate-ether to give 4.2 g (54%) of pure 5-[[3,5-Bis-(1,1-dimethylethyl)-4-hydroxyphenyl]methylene]-2-]hydroxy(1-methylethyl)amino]-4(5H)-thiazolidinone, (Z)-, mp 208° C. (dec).

Anal. for $C_{21}H_{30}N_2O_3S$: Calcd: C, 64.58; H, 7.74; N, 7.17. Found: C, 64.52; H, 7.67; N, 6.92.

EXAMPLE 9

[5-[[3,5-Bis(1,1-dimethylethyl)-4-hydroxyphenyl]methylene]-4,5-dihydro-4-oxo-2-thiazolyl]cyanamide A solution of cyanamide (5.04 g, 0.12 mole) and potassium-t-butoxide (12.28 g, 0.11 mole) in ethanol (1 L) is stirred at room temperature for 15 minutes. 5-[(3,5-Bis(1,1-dimethylethyl)-4-hydroxyphenyl)methylene]-2-(methylthio)-4(5H)-thiazolone (36.36 g, 0.1 mole) is then added to the solution and the mixture is refluxed with stirring for 23 hours. After removal of the solvent (~650 mL), the cooled reaction mixture is poured into a mixture of ice-water containing 1N hydrochloric acid. The solid is filtered, washed with water and then dissolved in ether-ethyl acetate. The organic layer is washed with water, dried and the solvent removed to give 35.7 g of a solid. The solid is recrystallized from methanol to give 25.1 g (70%) of pure [5-[[3,5-Bis(1,1-dimethylethyl)-4-hydroxyphenyl]-methylene]-4,5-dihydro-4-oxo-2-thiazolyl]cyanamide, mp 240°-242° C.

Anal. for $C_{19}H_{23}N_3O_2S.0.2CH_3OH$: Calcd: C, 63.38; H, 6.59; N, 11.55; S, 8.81. Found: C, 63.18; H, 6.70; N, 11.55; S, 8.75.

EXAMPLE 9B

[5-[[3,5-Bis(1,1-dimethylethyl)-4-hydroxyphenyl]methylene]-4,5-dihydro-4-oxo-2-thiazolyl]cyanamide, choline salt To a solution of [5-[(3,5-bis(1,1-dimethylethyl)-4-hydroxyphenyl)methylene]-4,5-dihydro-4-oxo-2-thiazolyl]cyanamide (12.7 g, 0.035 mole) is added choline bicarbonate (12.1 g, 0.034 mole, 46.6% aqueous). The mixture is refluxed for two hours. After removal of the solvent, the residue is digested with ethyl acetate, then cooled and the precipitate is separated by filtration, washed with ethyl acetate to give 15 g of pure product, mp 189°–190° C. It is recrystallized from methanol-ethyl acetate to give 14.02 g (89.3%) of a white crystalline analytically pure [5-[[3,5-Bis(1,1-dimethylethyl)-4-hydroxyphenyl]methylene]-4,5-dihydro-4-oxo-2-thiazolyl]cyanamide, chlorine salt, mp 189°–190° C.

Anal. for $C_{19}H_{23}N_3O_2S \cdot C_5H_{14}NO$: Calcd: C, 62.58; H, 7.88; N, 12.16; S, 6.96. Found: C, 62.53; H, 7.86; N, 12.21; S, 7.14.

EXAMPLE 10

5-[[3,5-Bis(1,1-dimethylethyl)-4-hydroxylphenyl]methylene]-2-[[2-(dimethylamino)ethyl]amino-4(5H)-thiazolone, (Z)-

A mixture of 5-[(3,5-bis(1,1-dimethylethyl)-4-hydroxyphenyl]methylene]-2-thioxo-4-thiazolidinone (6.99 g, 0.02 mole), N,N-dimethylaminoethylamine (5.29 g, 0.06 mole), and ethanol (250 mL) is refluxed with stirring for 7.5 hours. The solvent is distilled off under reduced pressure and the residue is recrystallized from toluene, to give 5.7 g of a solid. The solid is recrystallized from methanol-ethyl acetate-toluene to give 3.4 g (42%) of pure 5-[[2,6-Bis(1,1-dimethylethyl)-4-hydroxylphenyl]methylene]-2-[[2-(dimethylamino)ethyl]amino-4(5H)-thiazolone, (Z)-, mp 209°–211° C.

Anal. for $C_{22}H_{33}N_3O_2S$: Calcd: C, 65.48; H, 8.24; N, 10.41. Found: C, 65.38; N, 8.34; S, 10.19.

Following the procedure of Examples 1–10, the following examples were prepared using appropriate corresponding starting materials.

Structure (shown above table):

3,5-di-tert-butyl-4-hydroxyphenyl-CH=C(—S—C(Y)=N—)—C(=O)—

| Example Number | Y | mp °C. | Yield % | Yield g | Method Example | Chromatography Elution Solvent | Purification Solvent | Empirical Formula | Analysis Calcd/Found C | H | N | S | Cl |
|---|---|---|---|---|---|---|---|---|---|---|---|---|---|
| 1C | NH₂·HCCO₂H ‖ HCCOOH | 198–200 | 45 | 6.1 | 1B | | methanol-ether | C₁₈H₂₄N₂O₂S·C₄H₄O₄ | 58.91; 58.76; | 6.29; 6.40; | 6.25; 6.54; | 7.15 7.15 | |
| 1D | NH₂·HCl | 237–239 | 69 | 9.31 | 1B | | methanol-ethyl acetate | C₁₈H₂₄N₂O₂S·HCl | 58.60; 58.66; | 6.82; 6.90; | 7.59; 7.54; | 8.69; 8.38; | 9.61 9.45 |
| 1E | NH₂·H₃C—⟨C₆H₄⟩—SO₃H | 205–207 | 96 | 14.5 | 1B | | methanol-ethyl acetate | C₁₈H₂₄N₂O₂S·C₇H₈O₃S | 59.50; 59.33; | 6.39; 6.59; | 5.55 5.46 | | |
| 1F | NH₂·HO—SO₃H | >140 | 23 | 2.2 | 1B | | methanol-ethyl acetate | C₁₈H₂₄N₂O₂S·C₂H₄O₄S | 52.38; 51.93; | 6.60; 6.70; | 6.11; 6.08; | 13.98 13.95 | |
| 3A | —N—CH₃ \| OCH₃ | 187–189 (dec) | 27 | 3.0 | 2 | CH₂Cl₂:CH₃OH = 95:5 | methylene chloride-eth. acet. | C₂₀H₂₈N₂O₃S | 63.80; 63.93; | 7.49; 7.10; | 7.74; 7.44; | 8.52 8.48 | |
| 4C | N—O⁻ \| H HO—(CH₂)₂N⁺(CH₃)₃ | 178–180 | 27 | 3.0 | 9B | | methanol-eth. acet. | C₁₈H₂₄N₂O₃S·C₅H₁₄NO | 61.17; 60.60; | 8.26; 8.35; | 9.30; 9.21; | 7.10 6.94 | |
| 6A | NH(CH₂)₃CO₂H | 239–240 | 65 | 2.7 | 6 | | tetrahydrofuran-ethyl acetate | C₂₂H₃₀N₂O₄S | 63.13; 63.04; | 7.22; 7.38; | 6.69; 6.68; | 7.66 7.60 | |
| 7A | NHC(CH₂OH)₃ | 157–162 | 23 | 1.5 | 7 | | dichloromethane-ether-hexane (chromatography elution solvent; dichloromethane:methanol = 9:1 | C₂₂H₃₂N₂O₅S | 60.53; 60.12; | 7.39; 7.34; | 6.42; 6.19; | 7.34 7.30 | |
| 8A | NHCN(CH₃)₂ ‖ NH | 293–295 | 63 | 7.0 | 8 | | dimethylformamide | C₂₁H₃₀N₄O₂S | 62.66; 62.33; | 7.51; 7.79; | 13.92; 13.76; | 7.96 8.20 | |

-continued structure: 3,5-di-tert-butyl-4-hydroxybenzylidene attached to C=C-S-C(=N)-Y with C=O group

| Example Number | Y | mp °C. | Yield % | Yield g | Method Example | Chromatography Elution Solvent | Purification Solvent | Empirical Formula | Analysis Calcd/Found C | H | N | S | Cl |
|---|---|---|---|---|---|---|---|---|---|---|---|---|---|
| 10A | NHCH$_2$CH$_2$OH | 266-267 | 25 | 1.85 | 10 | | methanol | C$_{20}$H$_{28}$N$_2$O$_3$S | 63.80; 63.58; | 7.50; 7.17; | 7.44; 7.19; | 8.51 8.52 | |
| 11 | SCH$_2$CO$_2$H | 191-192 | 51 | 5.93 | 5 | | ether-toluene | C$_{20}$H$_{25}$NO$_4$S$_2$ | 58.94; 58.87; | 6.18; 6.40; | 3.44; 3.35; | 15.74 15.65 | |
| 12 | NCH(CH$_3$)CO$_2$H | 281 (dec) | 30 | 2.45 | 6 | | tetrahydrofuran-eth. acetate | C$_{21}$H$_{28}$N$_2$O$_4$S | 62.35; 62.61; | 6.98; 6.86; | 6.92; 6.67; | 7.93 7.78 | |
| 13 | N(cyclohexyl)-OH | 213-215 (dec) | 29 | 2.5 | 8 | CH$_2$Cl$_2$:CH$_3$OH | methylene chloride-eth. acetate-hexane | C$_{24}$H$_{34}$N$_2$O$_3$S | 66.94; 66.67; | 7.96; 7.88; | 6.50; 6.39; | 7.45 7.39 | |
| 14 | SCH(CH$_3$)(CH$_3$) | 154-155 | 27 | 10.5 | 5 | | toluene-hexane | C$_{21}$H$_{29}$NO$_2$S$_2$ | 64.41; 64.81; | 7.46; 7.45; | 3.58; 3.29; | 16.38 16.59 | |
| 15 | CH(CN)CNH$_2$=O | 274-276 | 10 | 1.1 | 9 | chloroform:methanol = 9:1 | tetrahydrofuran-ethanol | C$_{21}$H$_{25}$N$_3$O$_3$S | 63.12; 62.70; | 6.31; 6.46; | 10.52; 10.12; | 8.03 7.79 | |
| 16 | NHC(NH)NH$_2$ | 267-268 | 31 | 6.0 | 8 | | methanol-ethanol | C$_{19}$H$_{26}$N$_4$O$_2$S 0.6 mole H$_2$O | 59.23; 59.61; | 7.12; 7.21; | 14.54; 14.12; | 8.32 8.42 | |
| 16A | NHC(NH)NH$_2$·HCl | 217-220 | 24 | 1.9 | 1B | | methanol-ethyl acetate | C$_{19}$H$_{26}$N$_4$O$_2$S·HCl | 55.53; 55.37; | 6.62; 6.70; | 13.63; 13.56; | 7.80; 7.74; | 8.63 8.77 |

-continued

Structure: 3,5-di-tert-butyl-4-hydroxyphenyl group connected via CH=C(C(=O)—)—S—C(=N—)—Y

| Example Number | Y | mp °C. | Yield % | Yield g | Method Example | Chromatography Elution Solvent | Purification Solvent | Empirical Formula | Analysis Calcd/Found C | H | N | S | Cl |
|---|---|---|---|---|---|---|---|---|---|---|---|---|---|
| 17 | NHOCH$_3$ | 245–246 | 77 | 2.69 | 8 | | methanol | C$_{19}$H$_{26}$N$_2$O$_3$S | 62.96; 62.65; | 7.23; 7.03; | 7.73; 7.44; | 8.84 8.89 | |
| 18 | NHCH$_3$ | 308–310 | 69 | 2.4 | 7 | | DMF-EtOAc | C$_{19}$H$_{26}$N$_2$O$_2$S | 65.86; 65.52; | 7.56; 7.73; | 8.09; 8.12; | 9.25 8.91 | |
| 18A | NHCH$_3$·HCl | 308–310 | 90 | 1.88 | 1B | | methanol-ether | C$_{19}$H$_{26}$N$_2$O$_2$S·HCl | 59.59; 59.04; | 7.11; 7.18; | 7.31; 7.01; | 8.37; 8.41; | 9.26 9.48 |
| 19 | NMe$_2$ | 247–249 | 77 | 2.76 | 7 | | methanol | C$_{20}$H$_{28}$N$_2$O$_2$S | 66.63 66.52; | 7.83; 7.75; | 7.77; 7.64; | 8.89 8.69 | |
| 19A | NMe$_2$·HCl | 247–249 | 75 | 1.8 | 1B | | methanol-ether | C$_{20}$H$_{28}$N$_2$O$_2$S·HCl | 60.51; 60.13; | 7.36; 7.37; | 7.06; 6.95; | 8.08; 8.04; | 8.93 8.87 |
| 32A | CH$_2$COOC$_2$H$_5$ | 225–227 | 37 | 1.5 | 32 | | methanol | C$_{22}$H$_{29}$NO$_4$S | 65.48; 65.39; | 7.24; 7.22; | 3.47; 3.53; | 7.95 7.81 | |

EXAMPLE 20

5-[[3,5-Bis(1,1-dimethylethyl)-4-hydroxyphenyl]methylene]-2-thioxo-4-oxazolidinone A mixture of 14.1 g (0.060 mole) of 3,5-di-tertbutyl-4-hydroxybenzaldehyde, 7.0 g (0.060 mole) of 2-thioxo-4-oxazolidinone, 17.4 g (0.21 mole) of sodium acetate, and 75 mL of acetic acid is stirred and heated at reflux under a nitrogen atmosphere for 20 hours. The cooled reaction mixture is added to 900 g of ice/water and the precipitated product filtered and washed with water. There is obtained 16.2 g (81% yield) of the oxazole product, suitable for further reaction.

A sample of the above crude product is chromatographed over silica gel, using elution with 2.5% ethyl acetate in dichloromethane followed by 25% ethyl acetate. The chromatography product is recrystallized from aqueous acetonitrile to yield the purified oxazolidinone, 5-[[3,5-bis(1,1-dimethylethyl)-4-hydroxyphenyl]methylene]-2-thioxo-4-oxazolidinone, mp 240° C. dec.

Anal. for $C_{18}H_{23}NO_3S$: Calcd: C, 64.83; H, 6.95; N, 4.20. Found: C, 65.00; H, 6.95; N, 4.17.

EXAMPLE 20A

An alternate procedure for the preparation of the above compound is as follows:

A mixture of 18.8 g (0.080 mole) of 3,5-di-tert-butyl-4-hydroxybenzaldehyde, 10.0 g (0.085 mole) of 2-thioxo-4-oxazolidinone, 28 mL of acetic acid, and 1.6 g (0.018 mole) of β-alanine in 80 mL of toluene is stirred and heated at reflux (with the inclusion of a Dean-Stark trap) for 4 hours. The precipitated crude product is filtered from the cooled reaction mixture and washed with hexane. Recrystallization from aqueous acetonitrile yields 11.1 g (41%) of the oxazolidinone product, identical with that prepared previously, i.e., 5-[[3,5-bis(1,1-dimethylethyl)-4-hydroxyphenyl]methylene]-2-thioxo-4-oxazolidinone.

EXAMPLE 21

5-[[3,5-Bis(1,1-dimethylethyl)-4-hydroxyphenyl]methylene]-2-(methylthio)-4(5H)-oxazolone A solution of 5.0 g (0.015 mole) of 5-[[3,5-bis(1,1-dimethylethyl)-4-hydroxyphenyl]methylene]-2-thioxo-4-oxazolidinone in 75 mL of tetrahydrofuran is cooled in ice and treated with 2.4 mL (1.7 g, 0.017 mole) of triethylamine. The mixture is stirred with ice cooling for 1 hour, then treated with 4.5 mL (10.3 g, 0.072 mole) of iodomethane. The ice bath is removed, and the mixture is stirred for an additional 24 hours. The reaction mixture is filtered, and the filter cake is washed several times with fresh tetrahydrofuran. The combined filtrates are evaporated, and the residue is chromatographed (silica gel, 2.5–5% ethyl acetate in dichloromethane elution) to yield 4.3 g (83%) of the purified thio ether, 5-[[3,5-bis(1,1-dimethylethyl)-4-hydroxyphenyl]methylene]-2-(methylthio)-4(5H)-oxazolone. A sample recrystallized from ethyl acetate:hexane had mp 164°–166° C.

Anal. for $C_{19}H_{25}NO_3S$: Calcd: C, 65.67; H, 7.25; N, 4.03. Found: C, 65.72; H, 7.20; N, 3.81.

EXAMPLE 22

[5-[[3,5-Bis(1,1-dimethylethyl)-4-hydroxyphenyl]methylene]-4,5-dihydro-4-oxo-2-oxazolyl]cyanamide A suspension of 0.38 g (0.0090 mole) of cyanamide in 50 mL of ethanol is cooled in ice and treated in small portions with 0.93 g (0.0083 mole) of potassium tert-butoxide. After stirring for 15 minutes, 2.6 g (0.0075 mole) of 5-[[3,5-bis(1,1-dimethylethyl)-4-hydroxyphenyl]methylene]-2-(methylthio)-4(5H)-oxazolone is added, followed by an additional 25 mL of ethanol. The mixture is stirred at reflux for 3 hours, then cooled to allow precipitation of the potassium salt of the product. The salt is filtered, washed several times with ether, suspended in 100 mL of cold water, and acidified with 1.0 mL of acetic acid. The mixture is stirred for 30 minutes and extracted with ethyl acetate (4×75 mL). The combined organic layers are washed with brine (2×150 mL), dried (anhydrous sodium sulfate), and evaporated to yield 1.0 g (38%) of the nitrile product, [5-[[3,5-bis(1,1-dimethylethyl)-4-hydroxyphenyl]methylene]-4,5-dihydro-4-oxo-2-oxazolyl]cyanamide. A sample recrystallized from hexane:ethyl acetate had mp 220° C. dec.

Anal. for $C_{19}H_{23}N_3O_3$: Calcd: C, 66.84; H, 6.79; N, 12.31. Found: C, 66.81; H, 6.83; N, 11.92.

EXAMPLE 23

[5-[[3,5-Bis(1,1-dimethylethyl)-4-hydroxyphenyl]methylene]-4,5-dihydro-4-oxo-2-oxazolyl]cyanamide choline salt A solution of 0.95 g (0.0028 mole) of the parent cyanamide of the title compound in 10 mL of methanol is treated with a solution of 1.0 g (0.0028 mole) of 46% aqueous choline bicarbonate in 5 mL of methanol. The mixture is digested for a few minutes on the steam bath, filtered, cooled, and the filtrate is evaporated. The residue is redissolved in methanol and reevaporated three times. The final glassy residue is stirred in 40 mL of hexane. Filtration yields 0.6% g (53%) of the choline salt, [5-[[3,5-bis-(1,1-dimethylethyl)-4-hydroxyphenyl]methylene]-4,5-dihydro-4-oxo-2-oxazolyl]cyanamide choline salt, mp 85° C. dec.

Anal. for $C_{24}H_{36}N_4O_4 \cdot 0.5H_2O$: Calcd: C, 63.55; H, 8.22; N, 12.35. Found: C, 63.92; H, 8.38; N, 12.31.

EXAMPLE 24

5-[[3,5-Bis(1,1-dimethylethyl)-4-hydroxyphenyl]methylene]-2-thioxo-4-imidazolidinone A mixture of 3,5-di-tert-butyl-4-hydroxybenzaldehyde (30.0 g, 128 mmols), 2-thiohydantoin (14.8 g, 128 mmols), and sodium acetate (36 g) in acetic acid (200 ml) is stirred under nitrogen and heated to reflux. After 24 hours the mixture is allowed to cool, and is stirred into water (2 L). After an hour the product is filtered off, washed three times with water, and dried. Recrystallization from acetonitrile gave the 5-[[3,5-bis(1,1-dimethylethyl)-4-hydroxyphenyl]methylene]-2-thioxo-4-imidazolidinone (24.6 g), mp 278°–279° C. (dec).

EXAMPLE 25

5-[[3,5-Bis(1,1-dimethylethyl)-4-hydroxyphenyl]methylene]-1,5-dihydro-2-(methylthio)-4H-imidazol-4-one Iodomethane (0.5 mL, 8 mmols) is added to a stirred suspension of 5-[[3,5-bis(1,1-dimethylethyl)-4-hydroxyphenyl]methylene]-2-thioxo-4-imidazolidinone (2.5 g, 7.5 mmols) and diisopropylethylamine (1.35 mL, 7.7 mmols) in ethanol (25 mL), and the mixture is stirred under an inert atmosphere at room temperature. After 5 hours the resultant solution is stirred into water (150 ml). After a hour the precipitate is filtered off, rinsed three times with water and dried to afford the 5-[[3,5-bis(1,1-dimethylethyl)-4-hydroxyphenyl]methylene]-1,5-dihydro-2-(methylthio)-4H-imidazol-4-one (2.6 g), mp 248°–249° C.

EXAMPLE 26

5-[[3,5-Bis(1,1-dimethylethyl)-4-hydroxyphenyl]methylene]-1-methyl-2-thioxo-4-imidazolidinone A mixture of 3,5-di-tert-butyl-4-hydroxybenzaldehyde (19.0 g, 81 mmols), 1-methyl-2-thioxo-4-imidazolidinone (10.6 g, 81 mmols) and beta-alanine (4.7 g, 53 mmols) in acetic acid (150 ml) is stirred under an inert atmosphere and heated to reflux. After 5 hours the mixture is allowed to cool, and is stirred into water (1.5 L). After an hour the product is filtered off, washed three times with water, and dried. Recrystallization from acetonitrile gave the 5-[[3,5-Bis(1,1-dimethylethyl)-4-hydroxyphenyl]methylene]-1-methyl-2-thioxo-4-imidazolidinone (17.5 g), mp 242°–244° C.

EXAMPLE 27

5-[[3,5-Bis(1,1-dimethylethyl)-4-hydroxyphenyl]methylene]-1,5-dihydro-1-methyl-2-(methylthio)-4H-imidazol-4-one Iodomethane (1.2 mL, 19 mmols) is added to a stirred suspension of 5-[[3,5-bis(1,1-dimethylethyl)-4-hydroxyphenyl]methylene]-1-methyl-2-thioxo-4-imidazolidinone (4.0 g, 12 mmols) and diisopropylethylamine (2.4 mL, 14 mmols) in ethanol (50 ml) and the mixture is stirred under an inert atmosphere at room temperature. After 18 hours the mixture is stirred in water (300 mL) for an hour and the product is filtered off, washed three times with water, and dried. Recrystallization from ethyl acetate gave the pure 5-[[3,5-Bis(1,1-dimethylethyl)-4-hydroxyphenyl]methylene]-1,5-dihydro-1-methyl-2-(methylthio)-4H-imidazol-4-one (3.0 g), mp 177°–179° C., retaining 0.25 equivalents of solvent of crystallization.

EXAMPLE 28

5-[[3,5-Bis(1,1-dimethylethyl)-4-hydroxyphenyl]methylene]-4,5-dihydro-1-methyl-4-oxo-1H-imidazol-2-yl-cyanamide Cyanamide (0.2 g, 4.8 mmols) is added to a solution of 5-[[3,5-bis(1,1-dimethylethyl)-4-hydroxyphenyl]methylene]-1,5-dihydro-1-methyl-2-(methylthio)-4H-imidazol-4-one (1.5 g, 3.9 mmols) and potassium tert-butoxide (0.5 g, 4.3 mmols) in ethanol (25 mL) and the mixture is stirred under an inert atmosphere and heated to reflux. After 2.5 hours the mixture is allowed to cool, and is then poured into water (200 mL), acidified with phosphoric acid, and stirred. After half an hour the product is filtered off, washed three times with water, and dried. Recrystallization from acetonitrile gave the 5-[[3,5-bis(1,1-dimethylethyl)-4-hydroxyphenyl]methylene]-4,5-dihydro-1-methyl-4-oxo-1H-imidazol-2-yl-cyanamide (0.7 g), mp 257°–259° C. (dec).

Starting Materials

1-Methyl-2-thioxo-4-imidazolidinone is prepared by the procedure of Kenyon, *J. Am. Chem. Soc.* 93 (1971) 5542.

All other reagents were obtained from commercial sources.

EXAMPLE 29

[5-[[3,5-Bis(1,1-dimethylethyl)-4-hydroxyphenyl]methylene]-4,5-dihydro-4-oxo-2-oxazolyl]guanidine A solution of 2.0 g (0.021 mole) of guanidine hydrochloride in 75 mL of ethanol is cooled in ice and treated in portions with 2.2 g (0.020 mole) of potassium tert-butoxide. The mixture is stirred for 15 minutes, and then rapidly filtered into a suspension of 4.6 g (0.013 mole) of 5-[[3,5-bis-(1,1-dimethylethyl)-4-hydroxyphenyl]methylene]-2-(methylthio)-4(5H)-oxazolone in 75 mL of ethanol. The new reaction mixture is stirred at reflux for 3 hours, then cooled and filtered. The filtrate is evaporated 50% and added to 500 g of ice and water. The precipitated solid is filtered, washed with water, and dissolved in 200 mL of ethyl acetate. The solution is washed with brine (3×200 mL), dried (anhydrous sodium sulfate), and evaporated. The residue is chromatographed over silica gel, using elution with 10% acetonitrile in ethyl acetate. The purified product, [5-[[3,5-bis(1,1-dimethylethyl)-4-hydroxyphenyl]methylene]-4,5-dihydro-4-oxo-2-oxazolyl]guanidine, is 2.6 g (55% yield). A sample recrystallized from aqueous acetonitrile has mp 258°-dec.

Calcd. for $C_{19}H_{26}N_4O_3$: Calcd: C, 63.66; H, 7.31; N, 15.63. Found: 63.93; H, 7.25; N, 15.57.

EXAMPLE 30

[5-[[3,5-Bis(1,1-dimethylethyl)-4-hydroxyphenyl]methylene]-4,5-dihydro-4-oxo-2-oxazolyl]guanidine methanesulfonate A solution of 1.80 g (0.0050 mole) of the parent guanidine derivative of the title compound in 80 mL of warm 2-propanol is treated with a solution of 0.50 g (0.0052 mole) of methanesulfonic acid in 50 mL of 2-propanol. The precipitate that forms is redissolved by the addition of a small amount of 2-propanol and hot water. The solution is filtered hot and allowed to slowly cool to room temperature to precipitate 0.76 g (33% yield) of the methanesulfonate salt, mp 278°-dec.

Calcd. for $C_{19}H_{26}N_4O_3 \cdot CH_4O_3S$: Calcd: C, 52.84; H, 6.65; N, 12.33. Found: C, 52.70; H, 6.75; N, 12.19.

EXAMPLE 31

5-[[3,5-Bis(1,1-dimethylethyl)-4-hydroxyphenyl]methylene]-4,5-dihydro-1-methyl-4-oxo-1H-imidazol-2-yl-guanidine Guanidine hydrochloride (1.7 g, 18 mmoles) is added to a mixture of 5-[[3,5-bis(1,1-dimethylethyl)-4-hydroxyphenyl]methylene)-1,5-dihydro-1-methyl-2-(methylthio)-4-H-imidazole-4-one (3.0 g, 8 mmoles) and potassium tert-butoxide (1.5 g, 13 mmoles) in ethanol (50 mL), and stirred and heated to reflux under an inert atmosphere. After 24 hours the mixture is allowed to cool, and is poured into water (300 mL) and stirred. After half an hour the product is filtered off, rinsed three times with water and dried. Recrystallization from ethanol/DMF gave pure 5-[[3,5-bis(1,1-dimethylethyl)-4-hydroxyphenyl]methylene)-4,5-dihydro-1- methyl-4-oxo-1H-imidazol-2-yl-guanidine (0.6 g), mp 288°-290° C. (dec).

Preparation of Intermediate: Methyl (4-oxo-2-thiazolidinylidene) Acetate (A mixture of E:Z isomers)

A mixture of potassium-tert-butoxide (112.2 g, 1 mole) and methanol (400 mL) is kept at −10 to −6° C. and a mixture of methyl thioglycolate (106.14 g, 1 mole) and methyl cyanoacetate (99.09 g, 1 mole) is added over a period of 20 minutes. When the addition is completed stirring is continued at ~ −6° C. for 20 minutes, then at room temperature for 1.5 hours. The mixture is diluted with ether (~1.5 l) and the precipitate is removed by filtration, washed with ether, and air dried. The precipitate is then dissolved in ice water and carefully acidified with 4N hydrochloric acid. The product is separated by filtration, washed with water, and dried to give 119 g of a white solid. It is recrystallized from tetrahydrofuran-ethyl acetate to give 80.95 g (47%) of analytically pure product, mp 171°-172° C.

Anal. Calcd. for $C_6H_7NO_3S$: C, 41.61; H, 4.07; N, 8.09.
Found: C, 41.56; H, 4.11; N, 8.05

EXAMPLE 32

Methyl [5-[[3,5-Bis(1,1-dimethylethyl)-4-hydroxyphenyl]methylene]-4-oxo-2-thiazolidinylidene]acetate (Double bond in position 5 is Z, double bond in 2 position is a mixture of E:Z isomers)

A mixture of 3,5-di-tert-butyl-4-hydroxybenzaldehyde (23.4 g, 0.1 mole), methyl [[4-oxo-2-thiazolidinylidene)acetate (17.52 g, 0.101 mole), piperidine (3 mL) and ethanol (1 L) is refluxed with stirring for 21 hours. The reaction mixture is then cooled and the precipitate is separated by filtration to give 31.4 g of a solid, mp 256°-258° C. It is recrystallized from tetrahydrofuran-ethyl acetate to give 19.4 g (50%) of analytically pure product which is methyl [5-[[3,5-bis(1,1-dimethylethyl)-4-hydroxyphenyl]methylene]-4-oxo-2-thiazolidinylidene]acetate, mp 257°-259° C.

Anal. Calcd. for $C_{21}H_{27}NO_4S$: C, 64.75; H, 6.99; N, 3.60; S, 8.23. Found: C, 64.59; H, 6.89; N, 3.65; S, 8.03

EXAMPLE 33

5-[[3,5-Bis(1,1-dimethylethyl)-4-hydroxyphenyl]methylene]-1,5-dihydro-2-(methylthio)-4H-imidazol-4-one A mixture of iodomethane (0.5 mL, 8 mmoles), 5-[[3,5-bis(1,1-dimethylethyl)-4-hydroxyphenyl]methylene]-2-thioxo-4-imidazolidinone (2.5 g, 7.5 mmoles) and diisopropylethylamine (1.35 mL, 7.7 mmoles) in 25 mL of ethanol is stirred at room temperature under $N_2$ for 18 hours, then stirred into 150 mL of water. The precipitate is filtered off, rinsed with water, and dried to afford the pure product (2.5 g) which is 5-[[3,5-bis(1,1-dimethylethyl)-4-hydroxyphenyl]methylene]-1,5-dihydro-2-(methylthio)-4H-imidazol-4-one, mp 248°-249° C.

EXAMPLE 34

5-[[3,5-Bis(1,1-dimethylethyl)-4-hydroxyphenyl]methylene]-1,5-dihydro-1-methyl-2-(methylthio)-4H-imidazol-4-one A mixture of iodomethane (0.7 mL, 11 mmoles), 5-[[3,5-bis(1,1-dimethylethyl)-4-hydroxyphenyl]methylene]-1-methyl-2-thioxo-4-imidazolidinone (2.5 g, 7 mmoles) and diisopropylethylamine (1.5 mL, 8.5 mmoles) in 25 mL of ethanol with enough tetrahydrofuran added to effect solution is stirred overnight under $N_2$ at room temperature, then stirred into 250 mL of ice water. The precipitate is filtered off, rinsed with water, dried, and recrystallized from ethyl acetate to afford the product (1.6 g) 5-[[3,5-bis(1,1-dimethylethyl)-4-hydroxyphenyl]methylene]-1,5-dihydro-1-methyl-2-(methylthio)-4H-imidazol-4-one, mp 177°-178° C., retaining 0.25 equivalent of solvent of recrystallization.

EXAMPLE 35

5-[[3,5-Bis(1,1-dimethylethyl)-4-hydroxyphenyl]methylene]-4,5-dihydro-1-methyl-4-oxo-1H-imidazol-2-yl]cyanamide A solution of 5-[[3,5-bis(1,1-dimethylethyl)-4-hydroxyphenyl]methylene]-1,5-dihydro-1-methyl-2-(methylthio)-4H-imidazol-4-one (1.5 g, 3.9 mmoles), potassium t-butoxide (0.5 g, 4.3 mmoles) and 25 mL of ethanol is treated with cyanamide (0.2 g, 4.8 mmoles) and heated under reflux for 2.5 hours. The mixture is stirred into 200 mL of water, acidified with phosphoric acid, and the precipitate filtered off, rinsed with water, dried, and recrystallized from acetonitrile to afford the pure product (0.7 g), which is 5-[[3,5-Bis(1,1-dimethylethyl)-4-hydroxyphenyl]methylene]-4,5-dihydro-1-methyl-4-oxo-1H-imidazol-2-yl]cyanamide, mp 257°-295° C. (dec).

EXAMPLE 36

N-[5-[[3,5-Bis(1,1-dimethylethyl)-4-hydroxyphenyl]methylene]-4,5-dihydro-1-methyl-4-oxo-1H-imidazol-2-yl]guanidine A mixture of 5-[[3,5-bis(1,1-dimethylethyl)-4-hydroxyphenyl]methylene]-1,5-dihydro-1-methyl-2-(methylthio)-4H-imidazol-4-one (3.0 g, 8 mmoles), guanidine hydrochloride (1.7 g, 18 mmoles) and 50 mL of ethanol is treated with potassium t-butoxide (1.5 g, 13 mmoles) and heated under reflux for 20 hours, then stirred into 400 mL of water. The precipitate is filtered off, rinsed with water, dried, and recrystallized from acetone to afford the product (1.4 g), mp 286°-287° C. (dec). A sample recrystallized from DMF/EtOH was analytically pure which is N-[5-[[3,5-bis(1,1-dimethylethyl)-4-hydroxyphenyl]methylene]-4,5-dihydro-1-methyl-4-oxo-1H-imidazol-2-yl]guanidine, mp 288°-290° C. (dec).

EXAMPLE 37

5-[1-[3,5-Bis(1,1-dimethylethyl)-4-hydroxyphenyl]ethylidene]-2,4-thiazolidinedione A mixture of 3,5-bis(1,1-dimethylethyl)-4-hydroxyacetophenone (Tet Lett. 1981, 5293) (4.0 g, 16 mmoles), 2,4-thiazolidinedione (3.0 g, 26 mmoles) and ammonium acetate (1.9 g, 25 mmoles) in 12 mL of toluene is stirred under $N_2$ and heated to reflux for 48 hours, then stripped of solvent by rotary evaporator. The residue is boiled briefly in 20 mL of methanol, cooled, and the precipitate filtered off, rinsed with methanol, and dried to afford the pure product of 5-[1-[3,5-bis(1,1-dimethylethyl)-4-hydroxyphenyl]-ethylene]-2,4-thiazolidinedione (3.7 g), mp 253°-254° C.

EXAMPLE 38

5-[1-[3,5-Bis(1,1-dimethylethyl)-4-hydroxyphenyl]ethylidene]-2-thioxo-4-thiazolidinone A mixture of 3,5-bis(1,1-dimethylethyl)-4-hydroxyacetophenone (20.2 g, 81 mmoles), rhodanine (11.8 g, 86 mmoles), and ammonium acetate (6.6 g, 86 mmoles) in 110 mL of toluene under $N_2$ is heated under reflux using a Dean and Stark trap for 3 days, additional ammonium acetate (3.0 g, 37 mmoles) is added, and heating continued for a total of 96 hours. The mixture is cooled in an ice bath and the precipitated product is filtered off, rinsed with toluene then ethanol and dried to afford gold-brown crystals (22.2 g), mp 244°–246° C. A sample recrystallized from acetonitrile was analytically pure, which is 5-[1-[3,5-bis(1,1-dimethylethyl)-4-hydroxyphenyl]ethylidene]-2-thioxo-4-thiazolidinone, mp unchanged.

EXAMPLE 39

5-1-[3,5-Bis(1,1-dimethylethyl)-4-hydroxyphenyl]ethylidene]-2-(methylthio)-4(5H)-thiazolone A mixture of 5-[1-[3,5-bis(1,1-dimethylethyl)-4-hydroxyphenyl]ethylidene]-2-thioxo-4-thiazolidinone (1.6 g, 4 mmoles), iodomethane (0.45 mL, 7 mmoles), and diisopropylethylamine (1.1 mL, 6 mmoles) in 20 mL of ethanol is stirred under $N_2$ at room temperature for 16 hours, then stirred into 200 mL of water. The precipitate is filtered off, rinsed with water, and dried to afford the product (1.4 g) of 5-[1-[3,5-bis(1,1-dimethylethyl)-4-hydroxyphenyl]-ethylidene]-2-(methylthio)-4(5H)-thiazolone, mp 206°–209° C. A sample recrystallized from acetonitrile was analytically pure, mp 224°–226° C.

EXAMPLE 40

[5-[1-[3,5-Bis(1,1-dimethylethyl)-4-hydroxyphenyl]ethylidene]-4,5-dihydro-4-oxo-2-thiazolyl]cyanamide Potassium t-butoxide (0.9 g, 8 mmoles) is added to a stirred suspension of 5-[1-[3,5-bis(1,1-dimethylethyl)-4-hydroxyphenyl]ethylidene]-2-(methylthio)thiazolone (2.5 g, 7 mmoles) in 30 mL of ethanol under $N_2$, followed by cyanamide (0.4 g, 10 mmoles), and the mixture is heated under reflux. After 2 hours the mixture is cooled, stirred in 200 mL of water, and acidified with $H_3PO_4$. The precipitate is filtered off, rinsed with water, and dried to afford the product (2.3 g). Recrystallization of a sample from acetonitrile gave the analytically pure material, which is [5-[1-[3,5-bis(1,1-dimethylethyl)-4-hydroxyphenyl]-ethylidene]-4,5-dihydro-4-oxo-2-thiazolyl]cyanamide, mp 229°–230° C.

EXAMPLE 41

N-[5-[1-[3,5-Bis(1,1-dimethylethyl)-4-hydroxyphenyl]ethylidene]-4,5-dihydro-4-oxo-2-thiazolyl]guanidine Potassium t-butoxide (1.2 g, 10 mmole) is added to a stirred suspension of 5-[1-[3,5-bis(1,1-dimethylethyl)-4-hydroxyphenyl]ethylidene]-2-(methylthio)thiazolone (2.5 g, 7 mmoles) in 30 mL of ethanol under $N_2$, followed by guanidine hydrochloride (1.4 g, 15 mmoles), and the mixture is heated under reflux. After 2 hours, the mixture is cooled, stirred into 200 mL of water, and the precipitate filtered off, rinsed with water, and dried to give the product (2.5 g). A sample recrystallized from ethanol/acetonitrile was analytically pure, which is N-[5-[1-[3,5-bis(1,1-dimethylethyl)-4-hydroxyphenyl]ethylidene]-4,5-dihydro-4-oxo-2-thiazolyl]guanidine, mp 277° C. (dec).

We claim:
1. A compound of the formula I

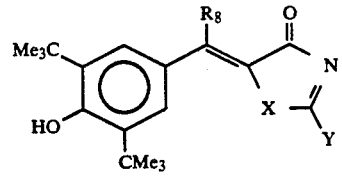

and a pharmaceutically acceptable base or acid addition salt thereof, wherein

Me is methyl;
X is O;
$R_8$ is hydrogen or methyl;
Y is

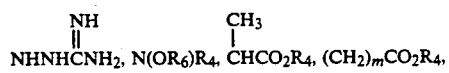

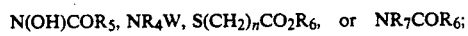

n is 1, 2 or 3;
m is 1 to 5;
$R_1$ and $R_2$ are independently H, lower alkyl, phenylalkyl, in which phenyl is unsubstituted or substituted as defined below, or $(CH_2)_nNR_6R_7$;
$R_3$ is H, lower alkyl, phenyl or phenyl substituted by one, two or three substituents of one or more of each of alkyl of one to four carbons, $OR_4$, $SR_4$,

hydroxymethyl, $NR_6R_7$, nitro or halogen;
$R_4$ is H or lower alkyl;
$R_5$ is lower alkyl, phenyl or phenyl substituted as defined above, or $CF_3$;
$R_6$ is H or lower alkyl;
$R_7$ is lower alkyl;
Z is O, S, NH, NCN; and
W is $CO_2R_7$ wherein $R_7$ is as defined above, $(CH_2)_mCOOH$,

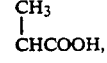

$(CH_2)_mOH$, or $C(CH_2OH)_3$.

2. A compound of claim 1 wherein Y is $SCH_3$.
3. A compound of claim 1 wherein Y is $SOCH_3$.
4. A compound of claim 1 wherein Y is $N(OR_6)R^4$.
5. A compound of claim 1 which is 5-[[3,5-Bis(1,1-dimethylethyl)-4-hydroxyphenyl]-methylene]-2-(methylthio)-4(5H)-oxazolone.
6. A compound of claim 1 which is [5-[[3,5-Bis(1,1-dimethylethyl)-4-hydroxyphenyl]-methylene]-4,5-dihydro-4-oxo-2-oxazolyl]cyanamide.
7. A compound of claim 1 which is [5-[[3,5-Bis(1,1-dimethylethyl)-4-hydroxyphenyl]-methylene]-4,5-dihydro-4-oxo-2-oxazolyl]cyanamide choline salt.

8. A compound of claim 1 which is [5-[[3,5-Bis(1,1-dimethylethyl)-4-hydroxyphenyl]-methylene]-4,5-dihydro-4-oxo-2-oxazolyl]guanidine.

9. A compound of claim 1 which is [5-[[3,5-Bis(1,1-dimethylethyl)-4-hydroxyphenyl]methylene]-4,5-dihydro-4-oxo-2-oxazolyl]guanidine methanesulfonate.

10. A pharmaceutical composition for use as an inhibitor of 5-lipoxygenase, cyclooxygenase, or both comprising a 5-lipoxygenase, cyclooxygenase, or both inhibiting amount of a compound of claim 1 with a pharmaceutically acceptable carrier.

11. A method for treating an inflammatory disease or condition in a human suffering therefrom which comprises administering a compound of claim 1 in unit dosage form.

* * * * *